US009060675B2

(12) United States Patent
Miyazono

(10) Patent No.: US 9,060,675 B2
(45) Date of Patent: Jun. 23, 2015

(54) RECEIVING APPARATUS AND CAPSULE ENDOSCOPE SYSTEM

(71) Applicant: OLYMPUS MEDICAL SYSTEMS CORP., Tokyo (JP)

(72) Inventor: Toru Miyazono, Tama (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 208 days.

(21) Appl. No.: 13/917,799

(22) Filed: Jun. 14, 2013

(65) Prior Publication Data

US 2014/0002623 A1      Jan. 2, 2014

Related U.S. Application Data

(63) Continuation of application No. PCT/JP2012/063531, filed on May 25, 2012.

(30) Foreign Application Priority Data

Jun. 2, 2011 (JP) ................................ 2011-124664
Jun. 2, 2011 (JP) ................................ 2011-124665

(51) Int. Cl.
  *A61B 1/00* (2006.01)
  *A61B 1/04* (2006.01)
  *H04B 7/08* (2006.01)
  *H04W 52/02* (2009.01)

(52) U.S. Cl.
  CPC ......... *A61B 1/00016* (2013.01); *A61B 1/00006* (2013.01); *A61B 1/00009* (2013.01); *A61B 1/041* (2013.01); *H04B 7/0811* (2013.01); *H04B 7/0877* (2013.01); *H04W 52/0241* (2013.01); *A61B 1/00036* (2013.01)

(58) Field of Classification Search
  None
  See application file for complete search history.

(56) References Cited

U.S. PATENT DOCUMENTS 6,236,674 B1    5/2001  Morelli et al.
7,961,658 B2    6/2011  Sakoda et al.
8,175,559 B2    5/2012  Homan et al.

(Continued)

FOREIGN PATENT DOCUMENTS

CN     101087220 A     12/2007
CN     101268634 A      9/2008

(Continued)

OTHER PUBLICATIONS

International Search Report from corresponding PCT/JP2012/063531, dated Jun. 19, 2012.

(Continued)

*Primary Examiner* — Dave Czekaj
*Assistant Examiner* — Nam Pham
(74) *Attorney, Agent, or Firm* — Scully, Scott, Murphy & Presser, PC

(57) ABSTRACT

A receiving apparatus includes: a plurality of receiving antennas capable of receiving transmission data which is wirelessly transmitted frame by frame and includes a preamble at a head; a switching unit that selectively switches a connection to any one of the plurality of receiving antennas; a preamble detector that detects the preamble of the transmission data output via the receiving antenna which is connected by the switching unit; and a control unit that controls whether or not to cause the preamble detector to be in a sleep condition based on a detection result by the preamble detector.

10 Claims, 15 Drawing Sheets

(56) References Cited

U.S. PATENT DOCUMENTS

| | | | |
|---|---|---|---|
| 8,345,089 B2 | 1/2013 | Shigemori et al. | |
| 2007/0066868 A1* | 3/2007 | Shikii | 600/118 |
| 2008/0318541 A1 | 12/2008 | Kimoto | |
| 2010/0130818 A1* | 5/2010 | Jung et al. | 600/109 |

FOREIGN PATENT DOCUMENTS

| | | | |
|---|---|---|---|
| EP | 0 757 451 A2 | 2/1997 | |
| EP | 1 702 554 A1 | 9/2006 | |
| EP | 1 790 278 A1 | 5/2007 | |
| EP | 1 928 107 A1 | 6/2008 | |
| JP | 2007-75161 A | 3/2007 | |
| JP | 2007-88860 A | 4/2007 | |
| JP | 2007-124142 A | 5/2007 | |
| JP | 2007-235927 A | 9/2007 | |
| JP | 2007-251775 A | 9/2007 | |
| JP | 2008-271052 A | 11/2008 | |
| WO | 2009/062188 A1 | 5/2009 | |

OTHER PUBLICATIONS

Japanese Office Action dated Sep. 17, 2013 from related Japanese Application No. 2013-518061, together with an English language translation.

Extended Supplementary European Search Report dated Sep. 24, 2014 from related European Application No. 12 79 3928.8.

Japanese Office Action dated Jan. 14, 2014 issued in JP 2013-518061.

* cited by examiner

FIG.13

| FRAME RATE (fps) | OPERATION START TIME |
|---|---|
| 4 | $T_1$ |
| 2 | $T_2$ |
| 1 | $T_3$ |
| 0.5 | $T_4$ |

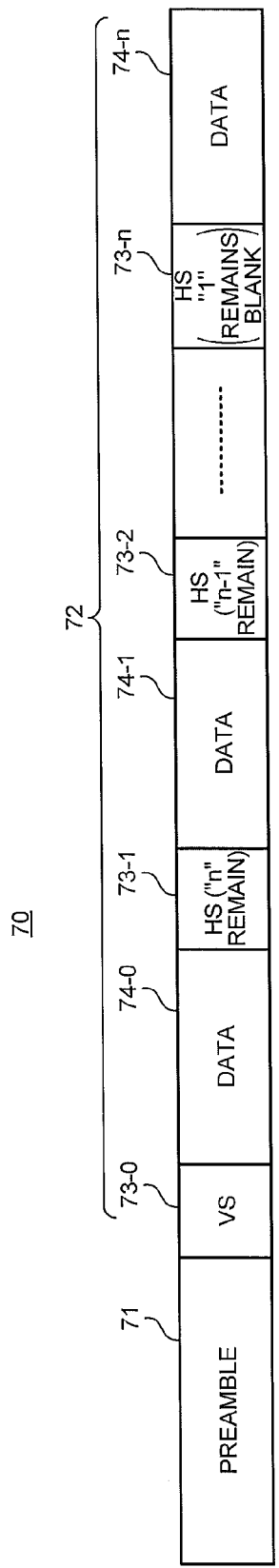

RECEIVING APPARATUS AND CAPSULE ENDOSCOPE SYSTEM

CROSS-REFERENCE TO RELATED APPLICATIONS

This application is a continuation of International Application No. PCT/JP2012/063531, designating the United States and filed on May 25, 2012 which claims the benefit of priority of the prior Japanese Patent Application No. 2011-124664 and the prior Japanese Patent Application No. 2011-124665, filed on Jun. 2, 2011, and the entire contents of the International application and the Japanese applications are incorporated herein by reference.

BACKGROUND OF THE INVENTION

1. Field of the Invention

The present invention relates to a receiving apparatus that receives transmission data wirelessly transmitted from a capsule endoscope introduced into an inside of a subject, and relates to a capsule endoscope system.

2. Description of the Related Art

Conventionally, a technique of receiving, by a receiving apparatus attached on an outside of a subject, image data which is captured by and wirelessly transmitted from a capsule endoscope that is inserted into the subject and captures images of an inside of the subject has been known (see Japanese Patent Application Laid-Open No. 2007-88860, for example).

A capsule endoscope transmits transmission data frame by frame at a specified frame rate. The transmission data is serial data including a preamble embedded at a head part and image data captured by the capsule endoscope.

The receiving apparatus includes a plurality of receiving antennas attached on a surface of a body of the subject. The receiving apparatus selects, after detecting the preamble of the transmission data, a receiving antenna whose received power is the largest of the plurality of receiving antennas. After that, the receiving apparatus detects a vertical synchronization signal included in the image data to start to receive the image data.

When the receiving apparatus is in an initial condition where transmission data is not received from the capsule endoscope or in a defect condition where transmission data is not received for a specified period of time after the latest reception, the receiving apparatus performs, after selecting a receiving antenna whose received power is the largest, a detection of the preamble included in the transmission data. When the preamble cannot be detected even after a lapse of a specified period of time after the selection of the receiving antenna, the receiving apparatus selects a receiving antenna again and then performs the preamble detection again. In this manner, the conventional receiving apparatus repeats the receiving antenna selection and the preamble detection until receiving transmission data when the receiving apparatus is in the initial condition or in the defect condition. In the receiving apparatus having such a configuration as explained above, it is possible to surely receive transmission data from the capsule endoscope.

SUMMARY OF THE INVENTION

According to an aspect of the present invention, a receiving apparatus includes: a plurality of receiving antennas capable of receiving transmission data which is wirelessly transmitted frame by frame and includes a preamble at a head; a switching unit that selectively switches a connection to any one of the plurality of receiving antennas; a preamble detector that detects the preamble of the transmission data output via a receiving antenna which is connected by the switching unit; and a control unit that controls whether or not to cause the preamble detector to be in a sleep condition based on a detection result by the preamble detector.

According to another aspect of the present invention, a capsule endoscope system includes: the receiving apparatus as set forth above, and a capsule endoscope that is introduced into a body of a subject and wirelessly transmits transmission data including image data obtained by capturing images of an inside of the subject, to the receiving apparatus.

The above and other features, advantages, and technical and industrial significance of this invention will be better understood by reading the following detailed description of presently preferred embodiments of the invention, when considered in connection with the accompanying drawings.

BRIEF DESCRIPTION OF THE DRAWINGS

FIG. 13 is a schematic diagram of frame rates stored in a storage unit of a receiving apparatus according to a third embodiment of the present invention and operation start time for each of the frame rates;

FIG. 16 is a schematic diagram of a configuration of transmission data transmitted from a capsule endoscope in a capsule endoscope system according to a fourth embodiment of the present invention.

DETAILED DESCRIPTION OF THE PREFERRED EMBODIMENTS

Exemplary embodiments of the present invention will be explained below.

First Embodiment

Figure 1:
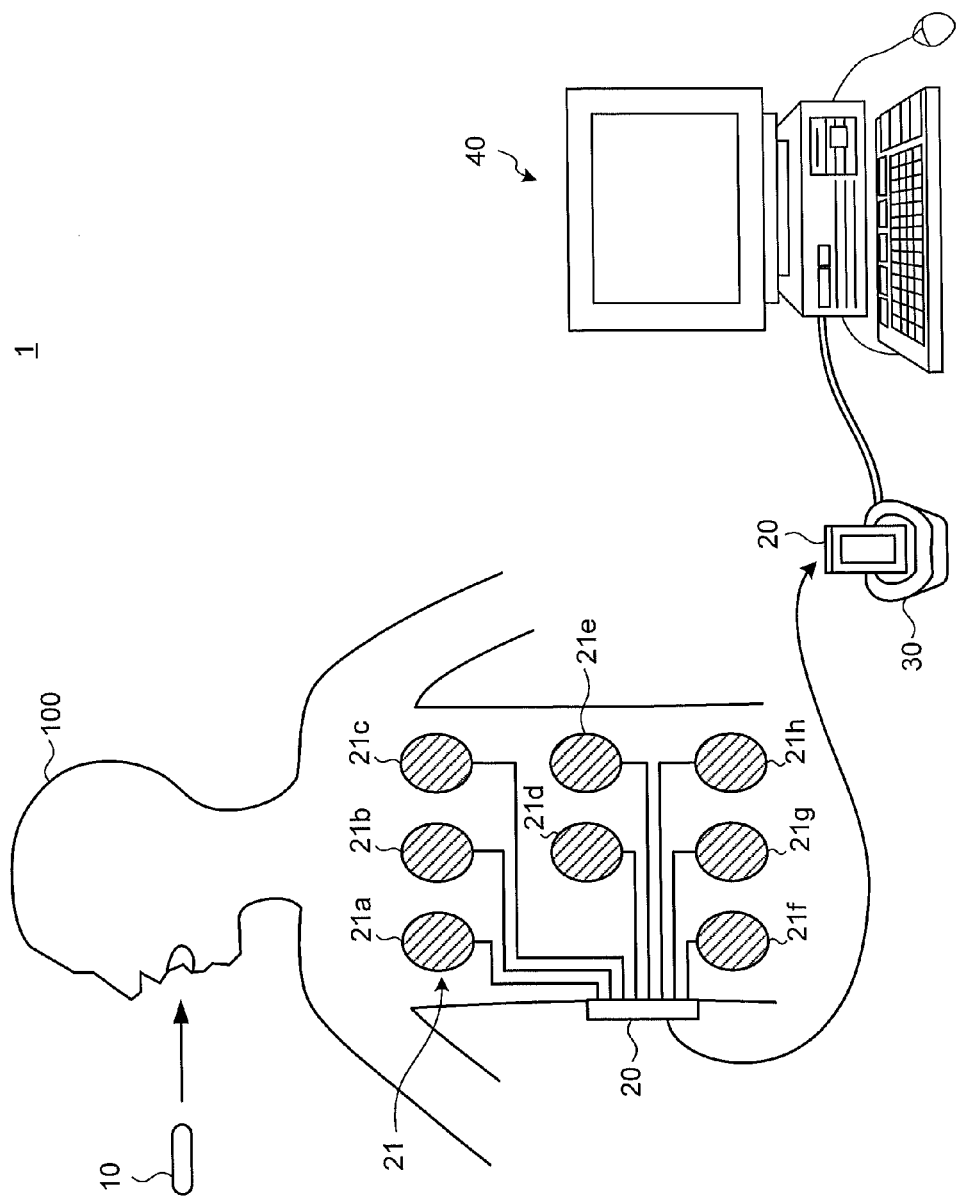
FIG. 1 is a schematic diagram of a brief configuration of a capsule endoscope system according to a first embodiment of the present invention.

FIG. 1 is a schematic diagram of a brief configuration of a capsule endoscope system according to a first embodiment of the present invention. A capsule endoscope system 1 shown in FIG. 1 includes: a capsule endoscope 10 that wirelessly transmits transmission data including image data of in-vivo images obtained by being inserted to an inside of a subject (patient) 100 and capturing images; a receiving apparatus 20 that receives the transmission data wirelessly transmitted from the capsule endoscope 10; a cradle 30 that receives the transmission data from the receiving apparatus 20 when the receiving apparatus 20 is inserted and attached thereto; and a display device 40 that is capable of transmitting and receiving data with the cradle 30 and displaying information such as in-vivo images included in the transmission data received from the receiving apparatus 20 via the cradle 30.

Figure 2:
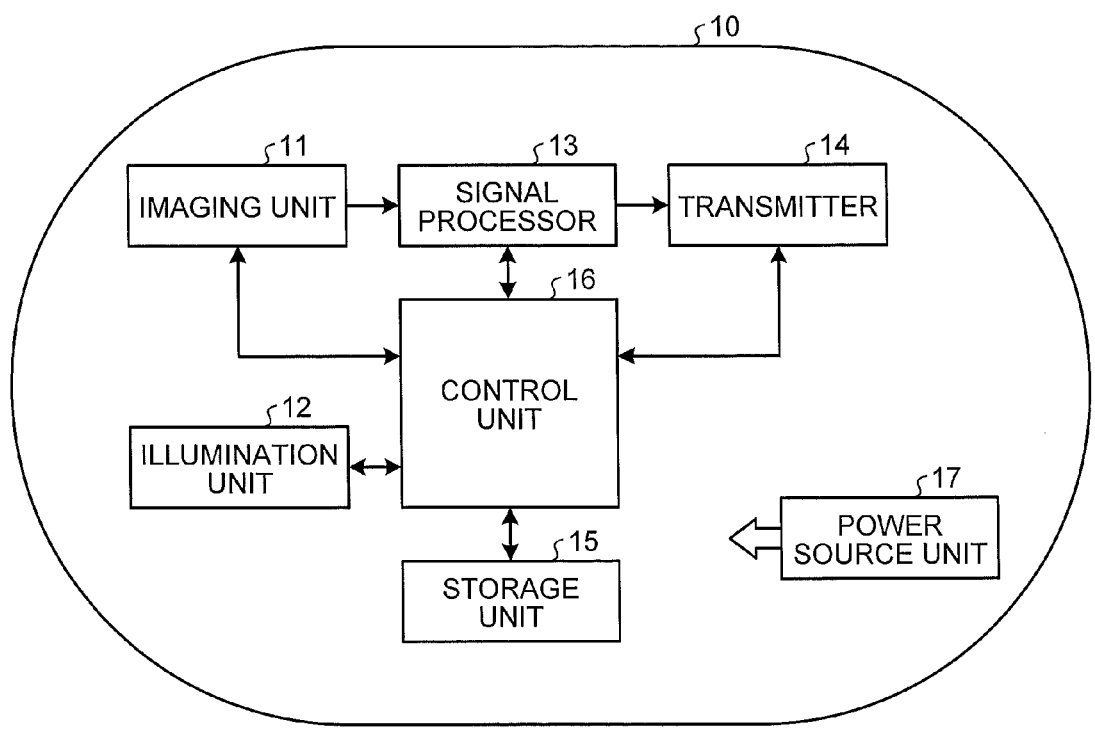
FIG. 2 is a block diagram of a brief configuration of the capsule endoscope.

A configuration of the capsule endoscope 10 will be explained first. The capsule endoscope 10 includes by sealing in a water-tight manner, in an inside of a casing having a capsule shape that can be inserted to an inside of a body cavity of the subject 100, functional components of various kinds for obtaining and wirelessly transmitting in-vivo images. FIG. 2 is a block diagram of a brief configuration of the capsule endoscope 10. As shown in FIG. 2, the capsule endoscope 10 includes: an imaging unit 11 that captures images of the inside of the subject 100 and performs a photoelectric conversion to generate an electrical signal; an illumination unit 12 that is realized by using a plurality of LEDs and illuminates the inside (the inside of the body cavity) including an area of a field of view of the imaging unit 11, of the subject 100; a signal processor 13 that performs a specified signal process on the electrical signal generated by the imaging unit 11; a transmitter 14 that wirelessly transmits transmission data including the image data generated by the signal processor 13 to the receiving apparatus 20; a storage unit 15 that stores information of various kinds; a control unit 16 that controls an operation of the capsule endoscope 10; and a power source unit 17 that supplies power to each unit of the capsule endoscope 10.

The imaging unit 11 includes an imaging element like CCD, CMOS, and the like and an image forming optical system in which an image is formed from a light condensed from the subject on a light receiving surface of the imaging element, and provided at an end part in a longitudinal direction of the casing, for example.

The signal processor 13 generates image data by performing signal processes such as amplification and A/D conversion on the signal output by the imaging unit 11.

The storage unit 15 is configured by using ROM, RAM, and the like and stores programs and setting data of various kinds for executing operations in the capsule endoscope 10.

The control unit 16 is configured by using CPU and the like and generally controls the operation of the capsule endoscope 10 by reading out and computing the programs of various kinds stored in the storage unit 15.

The capsule endoscope 10 with the above-explained configuration, after being swallowed from a mouth of the subject 100, travels in an inside of digestive canal including the esophagus, the stomach, the small intestine, the large intestine, and the like of the subject 100 according to a peristaltic motion and the like of organs. During this travelling, the imaging unit 11 of the capsule endoscope 10 sequentially captures images of the inside of the digestive canal at specified time intervals.

Figure 3:
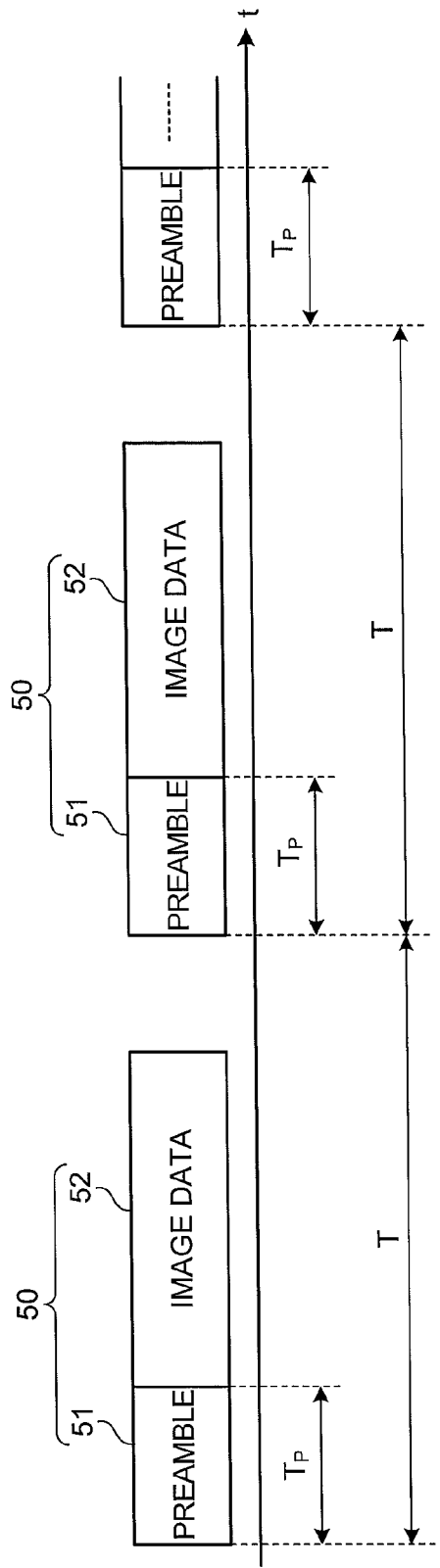
FIG. 3 is a schematic diagram of a configuration of transmission data transmitted from the capsule endoscope.

FIG. 3 is a schematic diagram of a configuration of transmission data transmitted from the capsule endoscope 10. Transmission data 50 shown in FIG. 3 is serial data including a preamble 51 locating at a head part and image data 52 which is main data following the preamble 51. The transmission data 50 is transmitted via the transmitter 14 in a specified transmission cycle T. In other words, the transmission data 50 is transmitted via the transmitter 14 at a frame rate 1/T. In FIG. 3, a reception time of the preamble 51 in a single piece of transmission data 50 is $T_p$. While a blank (a state where no signal is present) is present between two adjacent frames of transmission data 50 as shown in FIG. 3, the blank may not be present more commonly. In this manner, a gap between the transmission cycle T of transmission data 50 and a transmission time of transmission data 50 can be arbitrarily set depending on the kind and the like of transmission data 50.

Figure 4:
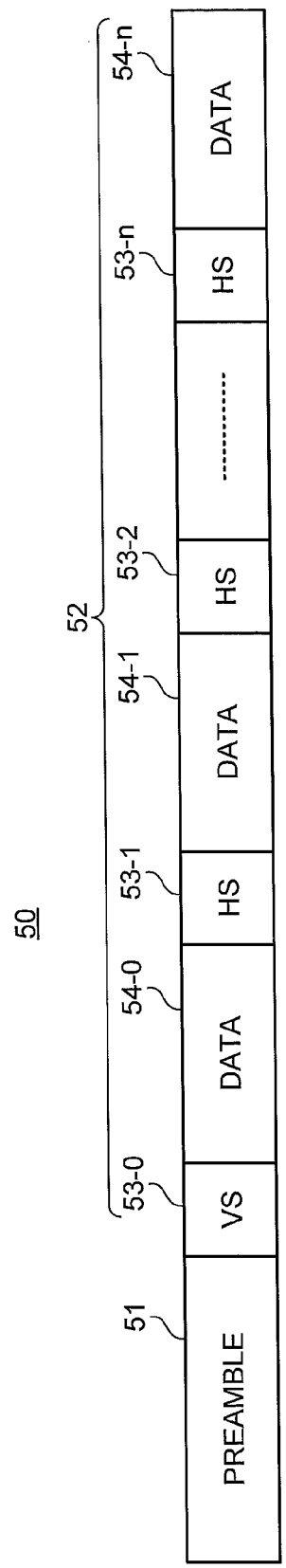
FIG. 4 is a schematic diagram of a detailed configuration of one frame of transmission data.

FIG. 4 is a schematic diagram of a detailed configuration of one frame of the transmission data 50. As shown in FIG. 4, a vertical synchronization signal (VS) 53-0 that indicates a start of image data is embedded at a head part of the image data 52. In the image data 52, data 54-0 in the first line is embedded after the vertical synchronization signal 53-0. A horizontal synchronization signal (HS) 53-1 that indicates a head of the second line follows the data 54-0 and is followed by data 54-1 in the second line. In the same manner, a horizontal synchronization signal and data in each line continues in series. In the case shown in FIG. 4, a horizontal synchronization signal 53-$n$ and data 54-$n$ in the n+1th line are embedded for data concerning the last line. The vertical synchronization signal 53-0 and the horizontal synchronization signals 53-1 and 53-$n$ are pulsed signals, for example.

Figure 5:
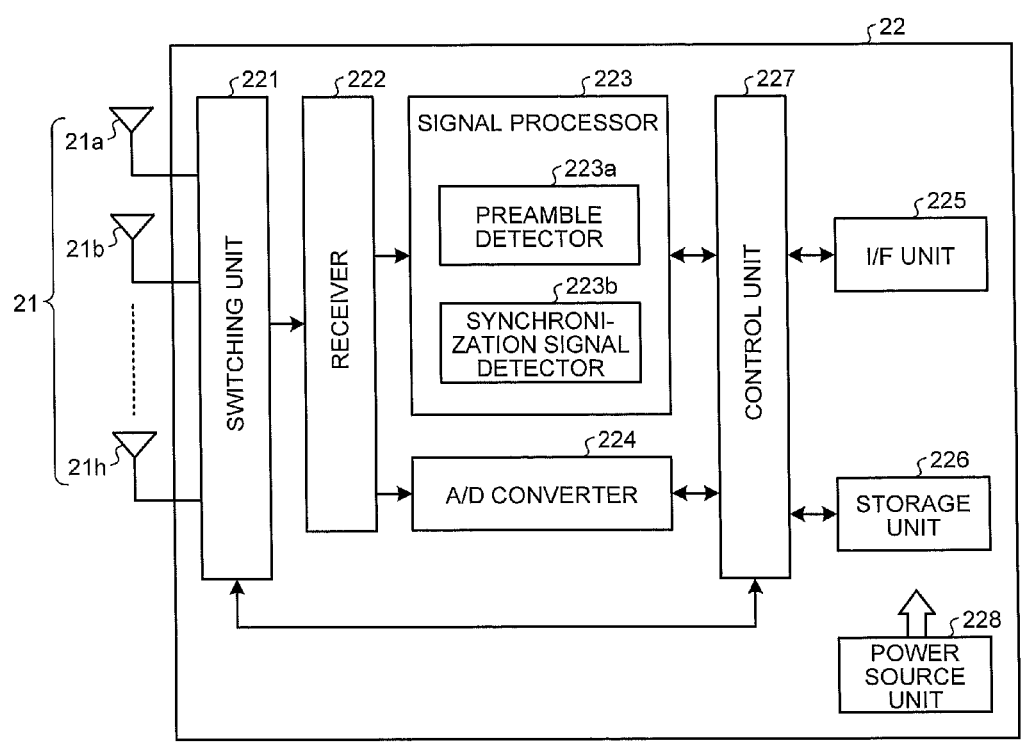
FIG. 5 is a block diagram of a configuration of a receiving apparatus according to the first embodiment of the present invention.

Next, a configuration of the receiving apparatus 20 will be explained. FIG. 5 is a block diagram of a configuration of the receiving apparatus 20. The receiving apparatus 20 shown in FIG. 5 includes an antenna unit 21 that is attached on a body surface or in a neighborhood of the body surface of the subject 100 and receives transmission data transmitted from the capsule endoscope 10 and a main body device 22 that obtains the transmission data output from the antenna unit 21.

The antenna unit 21 includes a plurality of receiving antennas 21$a$ to 21$h$. The plurality of receiving antennas 21$a$ to 21$h$ each are realized by using a loop antenna, for example and placed at specified positions on the body surface or in the neighborhood of the body surface of the subject 100. The specified positions are, for example, determined in accordance with organs which are the travelling route of the capsule endoscope 10, in the subject 100. While reference will be made to the case where the antenna unit 21 includes eight receiving antennas in the first embodiment, the number of receiving antennas is not limited to eight.

The main body device 22 includes a switching unit 221 that selectively switches a connection to any one of the receiving antennas 21$a$ to 21$h$, a receiver 222 that amplifies for demodulation transmission data as a wireless signal input via the receiving antenna connected by the switching unit 221, a signal processor 223 that performs a specified signal process on the transmission data received by the receiver 222, an A/D converter 224 that performs an A/D conversion with respect to a field intensity of the wireless signal amplified by the receiver 222, an I/F unit 225 that serves as a communication interface with an external device such as the cradle 30 which is electrically connected to the receiving apparatus 20, a storage unit 226 that stores information of various kinds, a control unit 227 that controls the operation of the receiving apparatus 20, and a power source unit 228 that supplies power to each unit of the receiving apparatus 20.

The signal processor 223 includes a preamble detector 223a that detects the preamble in the transmission data and a synchronization signal detector 223b that detects a synchronization signal (a vertical synchronization signal and a horizontal synchronization signal) in the transmission data. The preamble detector 223a is able to shift to a sleep condition under the control of the control unit 227. In the case of image data, a synchronization signal includes a vertical synchronization signal indicating a start position of data and a horizontal synchronization signal indicating a start position of each scan line.

The storage unit 226 is configured by using ROM, RAM, and the like and stores programs of various kinds for executing operations in the receiving apparatus 20 and setting data of various kinds including a frame rate (1/T) of the transmission data. Here, an interface to which a portable recording medium such as USB memory and CompactFlash (Registered Trademark) can be inserted and attached may be provided in the receiving apparatus 20 and the portable recording medium inserted and attached to the interface may be configured to function as the storage unit 226.

The control unit 227 is configured by using CPU and the like and generally controls the operation of the receiving apparatus 20 by reading out and computing the programs of various kinds stored in the storage unit 226.

Next, a configuration of the display device 40 will be explained. The display device 40 is realized by a workstation, a personal computer, and the like equipped with a display screen such as a monitor. The display device 40 can be connected to the cradle 30 and obtains the data received by the receiving apparatus 20 via the cradle 30. Here, the data received by the receiving apparatus 20 may be recorded in the portable recording medium and the portable recording medium may be inserted and attached to the display device 40 to receive and transmit the data. Besides, the reception and transmission of the data between the receiving apparatus 20 and the display device 40 may be performed by a wireless communication, without using the cradle 30.

Figure 6:
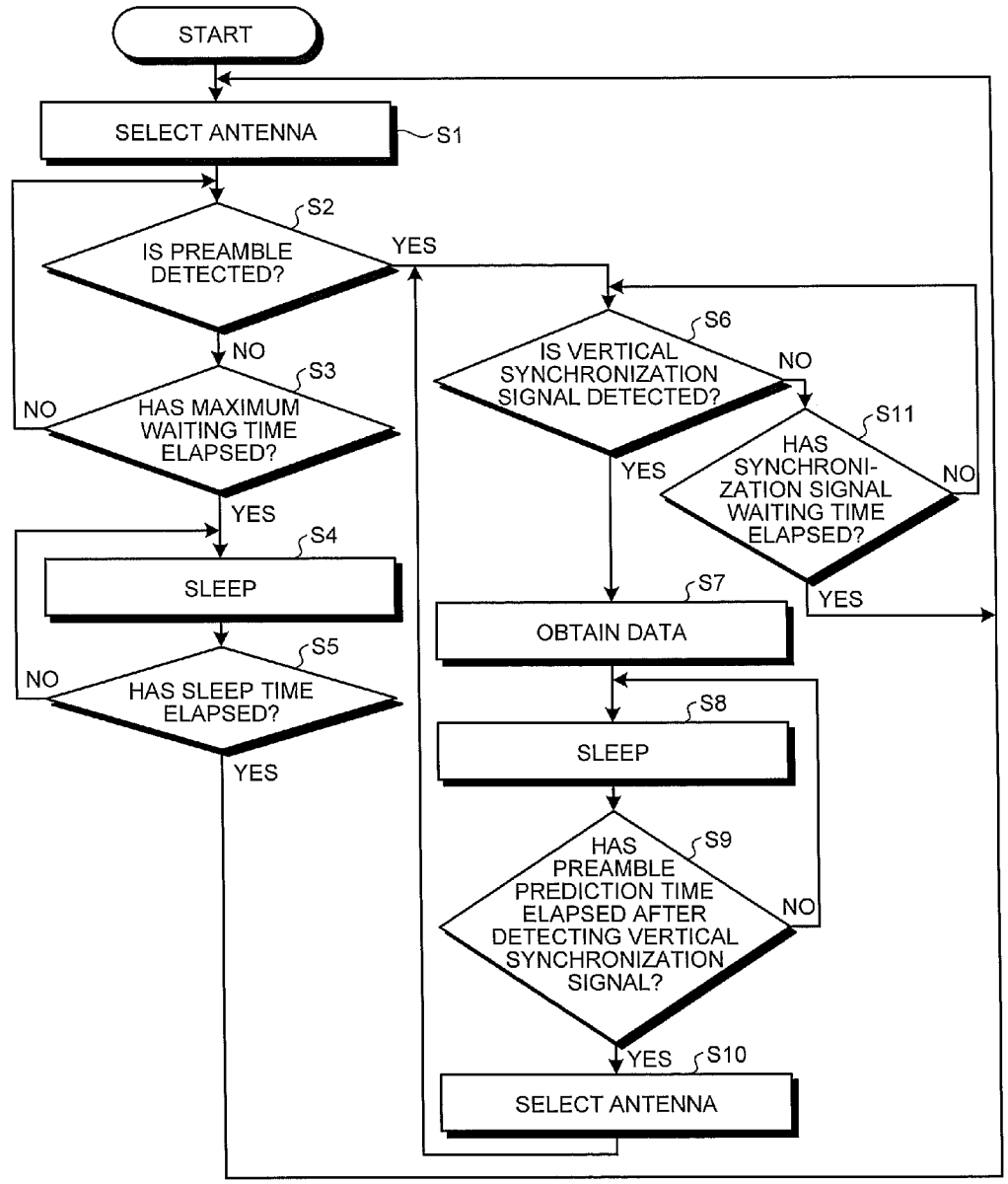
FIG. 6 is a flowchart of an outline of an operation of the receiving apparatus according to the first embodiment of the present invention.

FIG. 6 is a flowchart of an outline of an operation of the receiving apparatus 20. In the flowchart, reference will be made to a case of starting from an initial condition where the preamble detector 223a does not detect a preamble after a power activation of the receiving apparatus 20.

First, the control unit 227 selects an antenna whose received strength is the largest of the receiving antennas 21a to 21h (step S1). Specifically, the control unit 227 selects an antenna whose received strength is the largest of the receiving antennas 21a to 21h based on a received strength signal, input via the A/D converter 224, of each receiving antenna while causing the switching unit 221 to sequentially switch the connection to the receiving antennas 21a to 21h at specified intervals, and transmits a signal of instructing the connection to the selected receiving antenna to the switching unit 221.

The control unit 227 then activates the preamble detector 223a to perform a preamble detection of the transmission data 50 transmitted from the capsule endoscope 10 (step S2). When the preamble detector 223a does not detect a preamble ("No" at step S2) and when a maximum waiting time after the activation has not elapsed ("No" at step S3), the preamble detector 223a continues the preamble detection. On the other hand, when the maximum waiting time has elapsed at step S3 ("Yes" at step S3), the control unit 227 causes the preamble detector 223a to shift to a sleep condition (step S4). The sleep condition here indicates a state where the preamble detector 223a is not activated under a condition where a power by the power source unit 228 is kept supplied.

After that, when a sleep time during which the sleep condition continues has elapsed ("Yes" at step S5), the receiving apparatus 20 returns to step S1. In contrast, when the sleep time has not elapsed ("No" at step S5), the receiving apparatus 20 returns to step S4.

Figure 7:
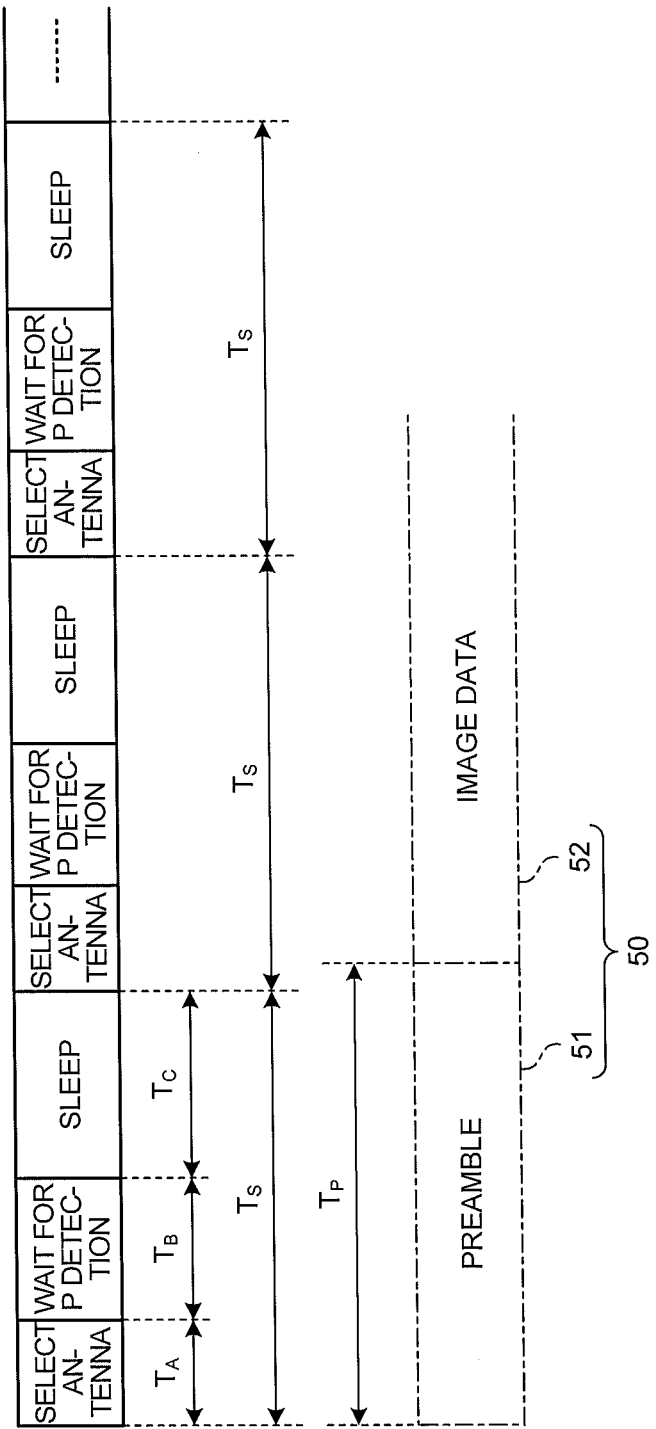
FIG. 7 is a schematic diagram of an operation flow of the receiving apparatus according to the first embodiment of the present invention.

FIG. 7 is a schematic diagram of an operation flow of the receiving apparatus 20. In FIG. 7, a lapse of time is shown rightward. When not receiving the transmission data 50, the receiving apparatus 20 repeats an operation of selecting a receiving antenna and causing the sleep condition through the wait condition for the preamble (P) detection. In the first embodiment, a total sum $T_S$ (=$T_A$+$T_B$+$T_C$) of an antenna selection time $T_A$ required for the receiving antenna selection, a maximum waiting time for preamble $T_B$, and a sleep time $T_C$ is set to be shorter than a reception time $T_P$ of the preamble 51 of a single piece of transmission data 50. Thus, it is possible in the receiving apparatus 20 to suppress power consumption by causing a shift to the sleep condition during the operation and also to surely detect a preamble.

Next, reference will be made to the case where the receiving apparatus 20 detects a preamble at step S2 ("Yes" at step S2). In this case, the synchronization signal detector 223b detects a vertical synchronization signal (step S6). When the synchronization signal detector 223b detects a vertical synchronization signal ("Yes" at step S6), the signal processor 223 obtains data that follows the vertical synchronization signal (step S7).

The control unit 227 then causes the preamble detector 223a to shift to the sleep condition (step S8).

After that, when a preamble prediction time has elapsed after the synchronization signal detector 223b had detected the vertical synchronization signal ("Yes" at step S9), the control unit 227 selects a receiving antenna whose received strength is the largest of the plurality of receiving antennas 21a to 21h (step S10) similarly to step S1 and returns to step S6. Here, the preamble prediction time indicates a time which is predicted based on the frame rate of the transmission data 50 stored in the storage unit 226 and which continues after the detection of the vertical synchronization signal until the start of the operation of selecting a receiving antenna with respect to transmission data 50 to be received next.

Figure 8:
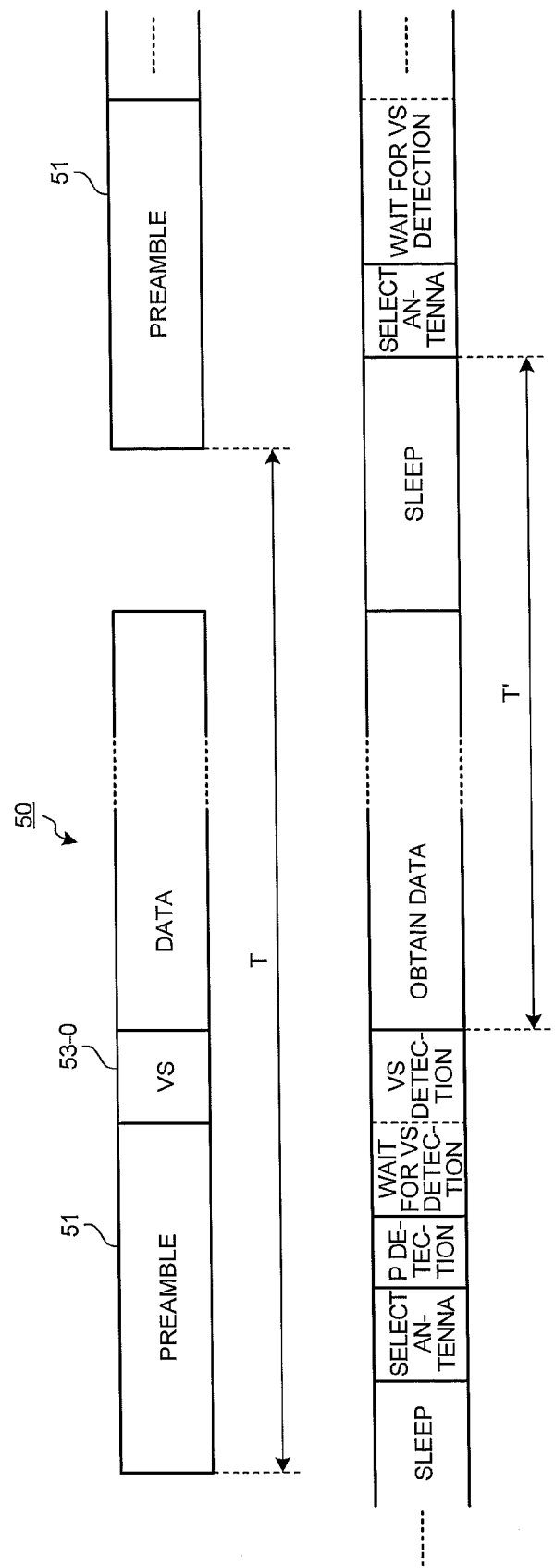
FIG. 8 is a schematic diagram of an outline of an operation of the receiving apparatus according to the first embodiment of the present invention, after detecting a preamble signal until selecting a receiving antenna.

FIG. 8 is a schematic diagram of an outline of an operation, after the preamble signal detection at step S2 until the receiving antenna selecting process at step S10, of the receiving apparatus 20. The transmission data 50 locating upward and an operation view locating downward in FIG. 8 are arranged along the same temporal axis in which time elapses rightward, and the time comes vertically into line. In FIG. 8, when the receiving apparatus 20 once obtains the transmission data 50, the control unit 227 starts the operation of selecting a receiving antenna at the point of the elapse of a preamble prediction time T' after the detection of the vertical synchronization signal. After that, the control unit 227 causes the synchronization signal detector 223b to detect a vertical synchronization signal. In this manner, the receiving apparatus 20, when obtaining the transmission data 50, never activates the preamble detector 223a unless the condition comes into a state where a preamble is not detected for equal to or more than a specified period of time after the latest preamble detection (defect condition). Therefore, it is possible to suppress power consumption due to the activation of the preamble detector 223a.

Continuously, the operation of the receiving apparatus 20 will be explained with reference to the flowchart in FIG. 6. When a vertical synchronization signal is not detected at step S6 ("No" at step S6), the receiving apparatus 20 returns to step S6 unless a specified waiting time for synchronization signal has elapsed ("No" at step S11). On the other hand, when the waiting time for synchronization signal has elapsed at step S11 ("Yes" at step S11), the receiving apparatus 20 returns to step S1.

Although, in the above description, reference has been made to the case of starting from the initial condition where the preamble detector 223a does not detect a preamble after a power activation of the receiving apparatus 20, the same processes (step S1 to S11) are performed even when the receiving apparatus 20 is in the defect condition.

According to the above-described first embodiment, since a period of next preamble is predicted based on a known frame rate after the detection of a preamble, it is not necessary to activate the preamble detector at all times. Thus, it is possible to surely obtain transmission data while more suppressing power consumption.

Since the total sum of the antenna selection time required for selecting a receiving antenna whose received strength is the largest, the maximum waiting time, and the sleep time is shorter than the reception time of a preamble in a single piece of transmission data in the initial condition or in the defect condition according to the first embodiment, it is possible to suppress power consumption due to the transition to the sleep condition and also to surely obtain transmission data without failure in taking data.

Second Embodiment

In a second embodiment of the present invention, a period of a preamble of transmission data transmitted by a capsule endoscope is divided into a first half and a second half in a manner distinguishable from each other. Here, the configuration of the capsule endoscope system is the same as the capsule endoscope system 1 explained in the first embodiment.

Figure 9:
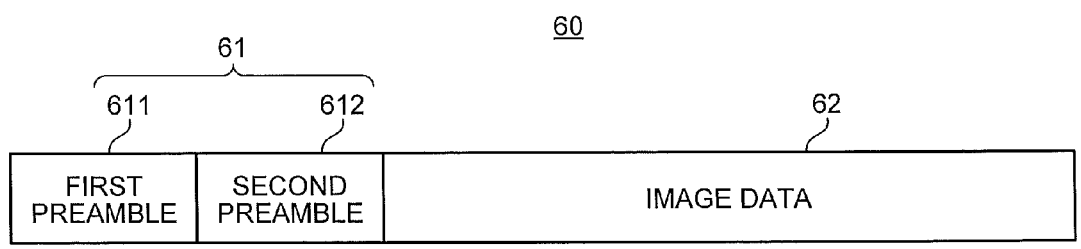
FIG. 9 is a schematic diagram of a configuration of one frame of transmission data transmitted and received between a capsule endoscope and a receiving apparatus in a second embodiment.

FIG. 9 is a schematic diagram of a configuration of one frame of transmission data to be transmitted and received between the capsule endoscope 10 and the receiving apparatus 20 in the second embodiment. Transmission data 60 shown in FIG. 9 includes a preamble 61 and image data 62. The preamble 61 includes a first preamble 611 and a second preamble 612. While information indicating data for a first half of a period of the preamble 61 is embedded in the first preamble 611, information indicating data for a second half of the period of the preamble 61 is embedded in the second preamble 612. A reception time of the first preamble 611 and a reception time of the second preamble 612 are equivalent. In other words, the period of the preamble 61 is divided into two along time.

Figure 10:
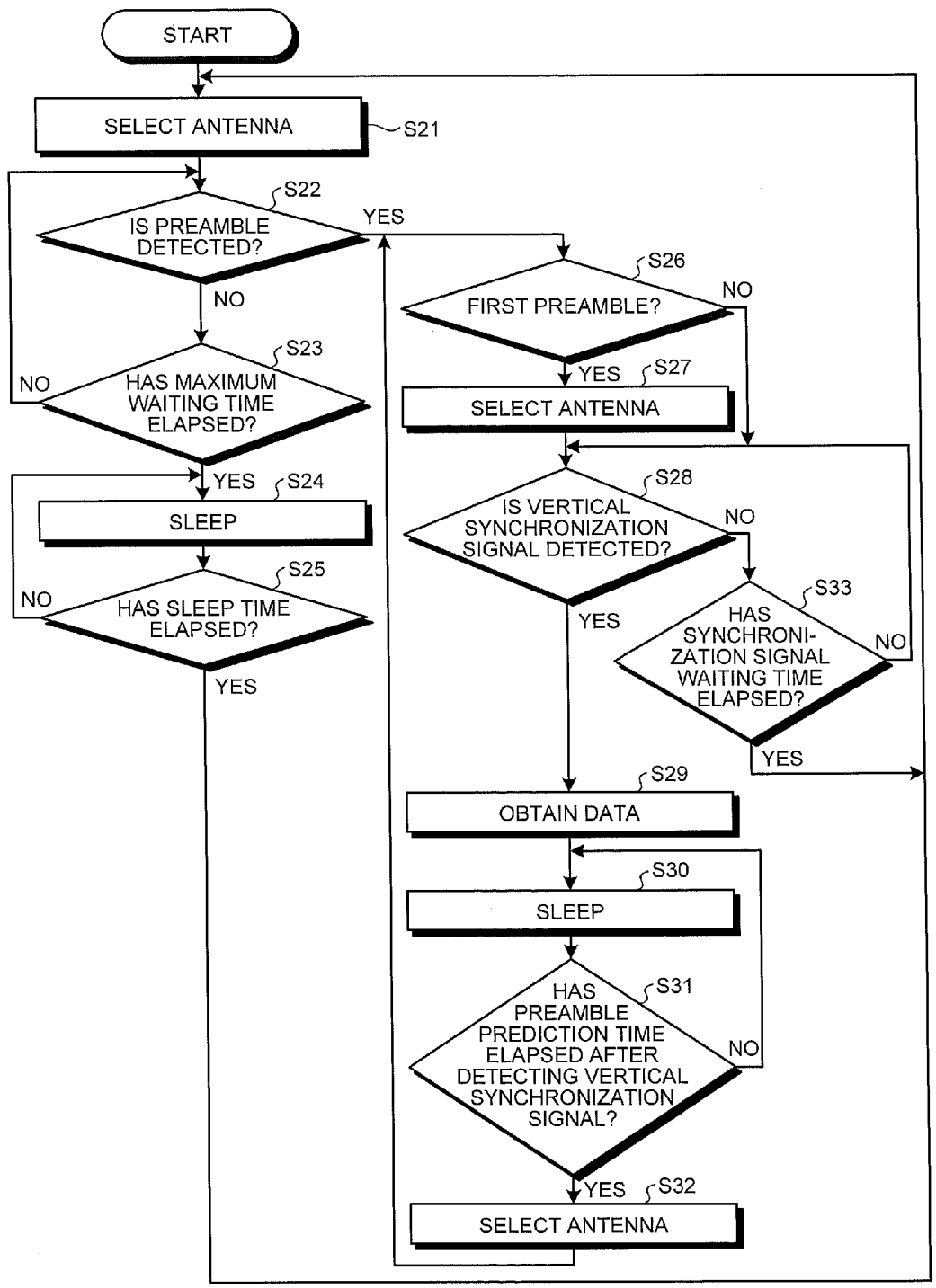
FIG. 10 is a flowchart of an outline of an operation of the receiving apparatus according to the second embodiment of the present invention.

FIG. 10 is a flowchart of an outline of an operation of a receiving apparatus 20 according to the second embodiment. In FIG. 10, steps S21 to S25 serially correspond to steps S1 to S5 in FIG. 6.

Reference will be made below to the case where the receiving apparatus 20 detects a preamble at step S22 ("Yes" at step S22). In this case, when data at a detected location is included in the first preamble 611 ("Yes" at step S26), the control unit 227 again selects a receiving antenna having the largest strength (step S27) and proceeds to step S28. In contrast, when the data at the detected location at step S26 is included in the second preamble 612 ("No" at step S26), the receiving apparatus 20 proceeds to step S28.

Figure 11:
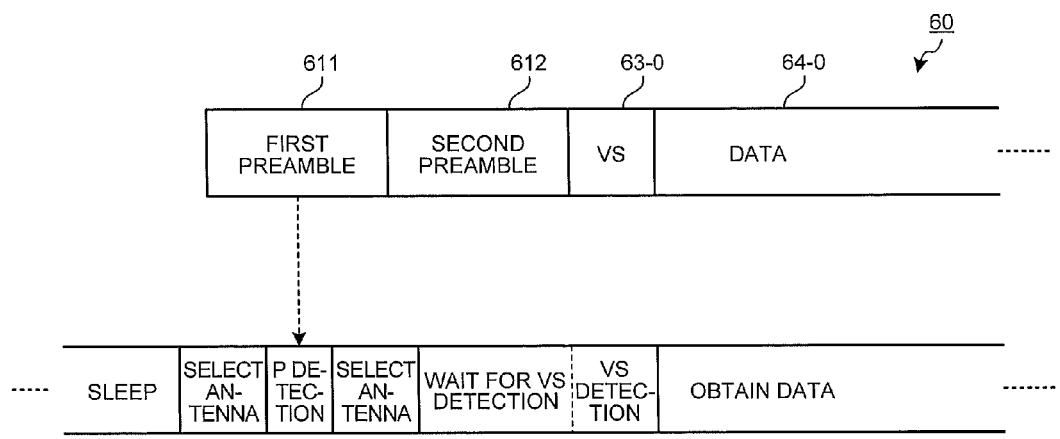
FIG. 11 is a schematic explanatory view of an operation (first example) when the receiving apparatus of the second embodiment of the present invention is in an initial condition or in a defect condition.
Figure 12:
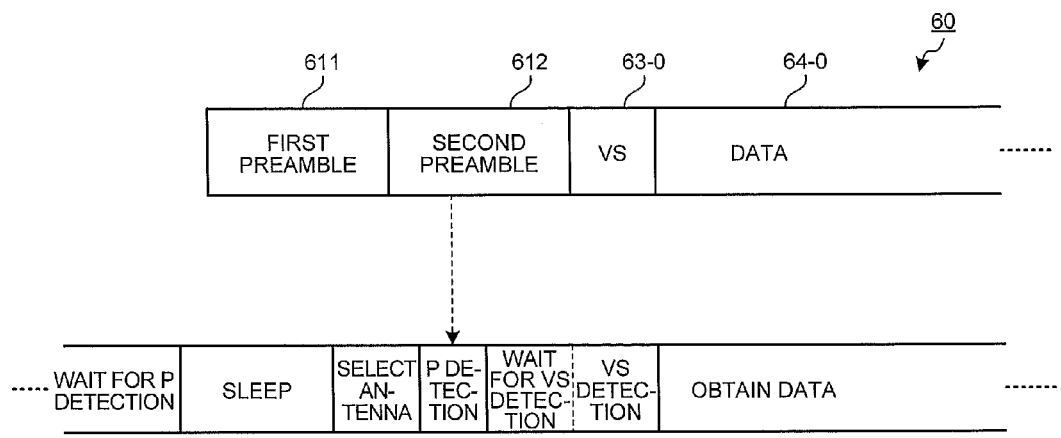
FIG. 12 is a schematic explanatory view of an operation (second example) when the receiving apparatus of the second embodiment of the present invention is in the initial condition or in the defect condition.

FIGS. 11 and 12 are schematic diagrams of operations of the receiving apparatus 20 according to the second embodiment. Specifically, FIG. 11 schematically shows an operation when the preamble that the receiving apparatus 20 first detects is the first preamble in the case where the receiving apparatus 20 is in the initial condition or in the defect condition. In contrast, FIG. 12 schematically shows an operation when the preamble that the receiving apparatus 20 first detects is the second preamble in the case where the receiving apparatus 20 is in the initial condition or in the defect condition. Here, the transmission data 60 (including the first preamble 611, the second preamble 612, a vertical synchronization signal 63-0, and data 64-0) locating upward and an operation view locating downward in FIGS. 11 and 12 are arranged along the same temporal axis in which time elapses rightward, and the time comes vertically into line.

When the preamble that the receiving apparatus 20 in the initial condition or in the defect condition first detects is the first preamble 611, there is a possibility that the selection of the receiving antenna with the largest strength signal is not performed at a time during the preamble period as shown in FIG. 11. In this case, there is a possibility that the receiving apparatus 20 cannot select a receiving antenna most suitable for receiving the transmission data 60. So, the receiving apparatus 20 again selects a receiving antenna after the detection of the first preamble.

In contrast, when the preamble that the receiving apparatus 20 in the initial condition or in the defect condition first detects is the second preamble 612, it is apparent that the selection of a receiving antenna is performed during the preamble period as shown in FIG. 12. In this case, the receiving apparatus 20 proceeds to a process of detecting a vertical synchronization signal by the synchronization signal detector 223b.

Steps S28 to S33 to be performed after step S27 explained above serially correspond to steps S6 to S11 in FIG. 6.

According to the above-described second embodiment of the present invention, it is possible to suppress power consumption similarly to the first embodiment.

Besides, since the preamble period is divided into the first preamble and the second preamble, and the switching unit sequentially switches the connection to the plurality of receiving antennas to select a receiving antenna whose received strength is the largest of the receiving antennas when the preamble detector detects the first preamble according to the second embodiment, it is possible to surely execute the operation of selecting a receiving antenna during the preamble period. Thus, it is possible to select a most suitable receiving antenna and surely obtain transmission data.

In the second embodiment, the reception time of the first preamble may not be the same as the reception time of the second preamble. A ratio of the reception time of the first preamble and the reception time of the second preamble may be arbitrarily set depending on conditions including a reception time of the original preamble, an antenna selection time, and the like. It is preferable, however, that the reception time of the first preamble is equal to or less than the reception time of the second preamble in order to secure a time for again selecting an antenna when the receiving apparatus detects the first preamble.

Third Embodiment

A receiving apparatus according to a third embodiment of the present invention has a configuration capable of dealing with transmission data whose frame rate changes in midstream. Specifically, the receiving apparatus according to the third embodiment stores, in a storage unit, a plurality of frame rates different from each other, detects a preamble in a manner of covering these frame rates, and obtains transmission data. Hence, it is possible in the receiving apparatus according to the third embodiment to receive transmission data transmitted from a capsule endoscope having a function of changing frame rates of transmission data. The configuration of the capsule endoscope except for what is explained here is the same as the configuration of the capsule endoscope system 1 explained in the first embodiment.

FIG. 13 shows frame rates stored in the storage unit 226 of the receiving apparatus 20 according to the third embodiment and operation start time for next frame detection determined for each of the frame rates. The operation start time mentioned here is a time after the receiving apparatus 20 detects a horizontal synchronization signal in the initial condition or in the defect condition until the receiving apparatus 20 starts to select a receiving antenna (A) during a preamble period of transmission data to be received next. As shown in FIG. 13, the storage unit 226 stores four frame rates, i.e., 4 (fps), 2 (fps), 1 (fps), and 0.5 (fps). The storage unit 226 also stores operation start times $T_1$, $T_2$, $T_3$, and $T_4$ respectively corresponding to the frame rates 4 (fps), 2 (fps), 1 (fps), and 0.5 (fps). Here, the operation start times $T_1$, $T_2$, $T_3$, and $T_4$ satisfy a relation "$T_1<T_2<T_3<T_4$". Here, the value and the number of the frame rates stored in the storage unit 226 are not limited to the case shown in FIG. 13.

Figure 14:
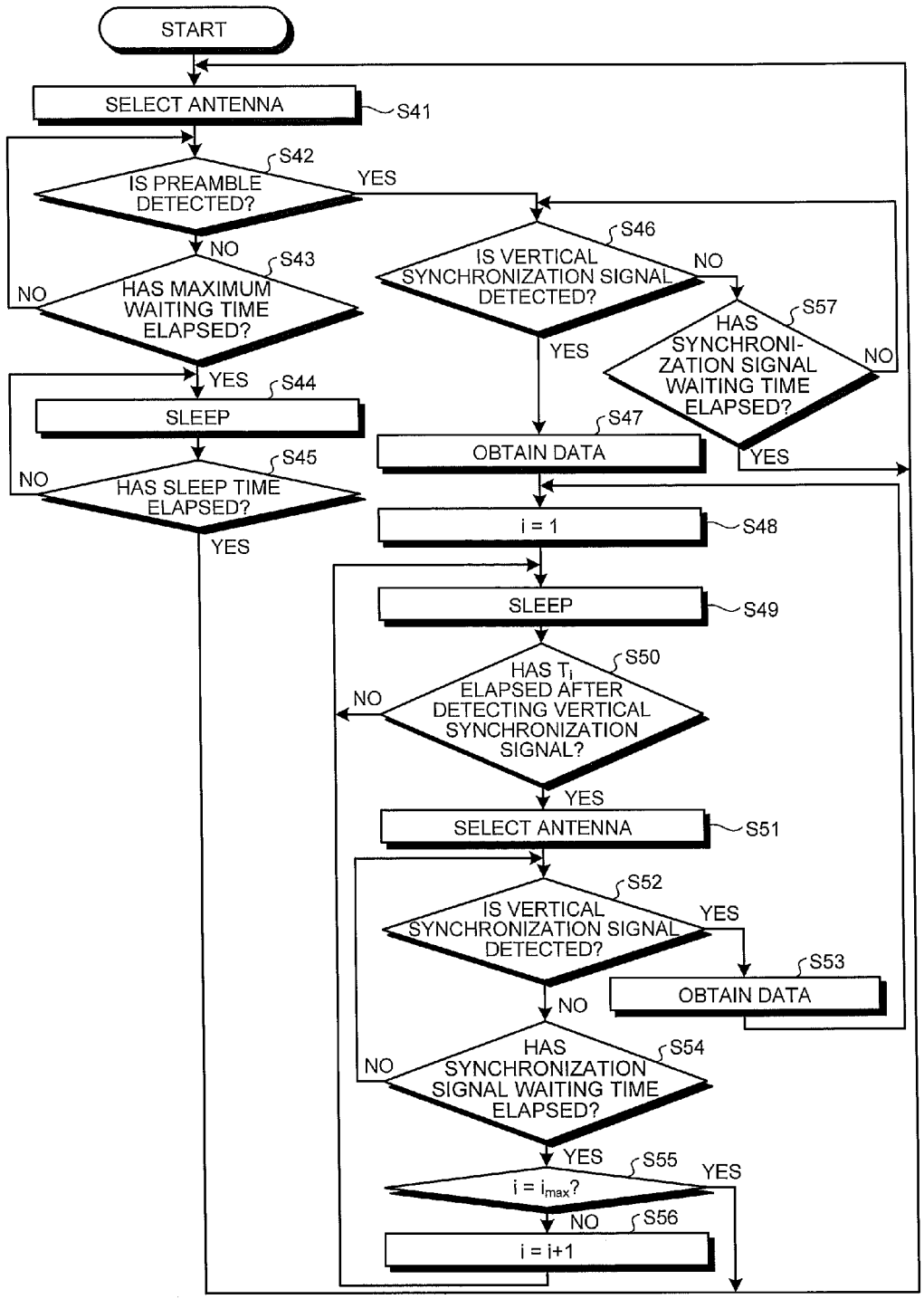
FIG. 14 is a flowchart of an outline of a process performed by the receiving apparatus according to the third embodiment of the present invention.

FIG. 14 is a flowchart of an outline of a process performed by the receiving apparatus according to the third embodiment of the present invention. In FIG. 14, processes from step S41 to step S45 serially correspond to steps S1 to S5 in FIG. 6.

Reference will be made below to the case where a preamble signal is detected at step S42 ("Yes" at step S42). In this case, the synchronization signal detector 223b detects a vertical synchronization signal (step S46). When the synchronization signal detector 223b detects a vertical synchronization signal ("Yes" at step S46), the signal processor 223 obtains data following the vertical synchronization signal (step S47).

The control unit 227 then sets an internal counter i for counting the number of repetition of the process to "1" (step S48) and causes the preamble detector 223a to a sleep condition (step S49).

After that, when an operation start time $T_i$ has elapsed after the synchronization signal detector 223b had detected the vertical synchronization signal ("Yes" at step S50), the control unit 227 selects a receiving antenna similarly to step S41 (step S51).

When the synchronization signal detector 223b then detects a vertical synchronization signal ("Yes" at step S52), the signal processor 223 obtains image data (step S53). After that, the receiving apparatus 20 returns to step S48.

On the other hand, when the vertical synchronization signal is not detected at step S52 ("No" at step S52), the receiving apparatus 20 proceeds to step S55 to be explained later when the synchronization signal waiting time has elapsed ("Yes" at step S54). In contrast, when the synchronization signal waiting time has not elapsed at step S54 ("No" at step S54), the receiving apparatus 20 returns to step S52.

At step S55, the control unit 227 determines whether or not the internal counter i is equivalent to a specified maximum value $i_{max}$. When the internal counter i is equivalent to the maximum value $i_{max}$ ("Yes" at step S55), the receiving apparatus 20 returns to step S41. On the other hand, when the internal counter i is not equivalent to the maximum value $i_{max}$ ("No" at step S55), the receiving apparatus 20 increments the internal counter i by one (step S56) and returns to step S49.

When the vertical synchronization signal is not detected at step S46 ("No" at step S46), the receiving apparatus 20 returns to step S41 when the synchronization signal waiting time has elapsed ("Yes" at step S57). On the other hand, when the synchronization signal waiting time has not elapsed ("No" at step S57), the receiving apparatus 20 returns to step S46.

Figure 15:
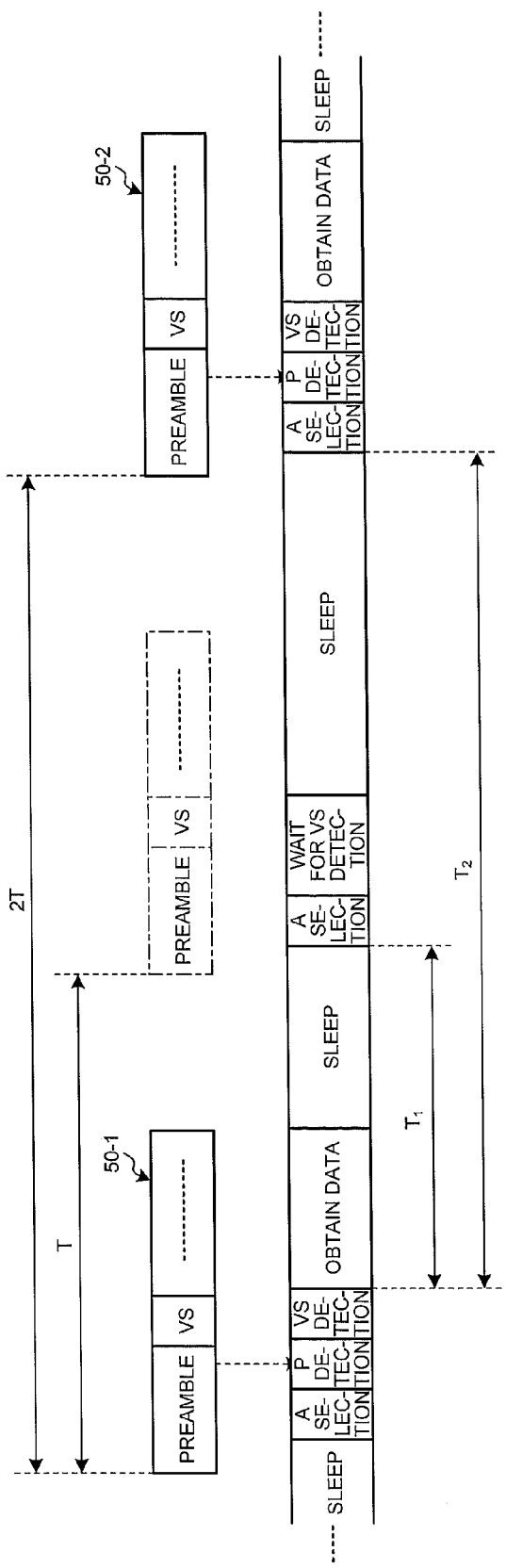
FIG. 15 is a schematic diagram of an outline of an operation performed by the receiving apparatus according to the third embodiment of the present invention.

FIG. 15 is a schematic diagram of an outline of an operation performed by the receiving apparatus 20 explained above. Transmission data locating upward and an operation view locating downward in FIG. 15 are arranged along the same temporal axis in which time elapses rightward, and the time comes vertically into line. Transmission data 50-1 at the leftmost location in FIG. 15 is assumed to be transmission data that the receiving apparatus in the initial condition or in the defect condition first receives.

In FIG. 15, the receiving apparatus 20 predicts an operation start time on the assumption that transmission data 50 to be received after the first-received transmission data 50-1 is transmitted at the maximum frame rate. Specifically, the maximum value of the plurality of frame rates stored in the storage unit 226 is 4 (fps). Therefore, a reception of the transmission data 50 which is predicted to be received next is configured to start at the time when T=0.25 (s) has elapsed after the reception start of the first transmission data 50. In this case, the control unit 227 causes the switching unit 221 to operate to start the process of selecting a receiving antenna at the time when the operation start time $T_1$ has elapsed after the synchronization signal detector 223b had detected the vertical synchronization signal of the transmission data 50-1. As shown in FIG. 15, the synchronization signal detector 223b cannot detect, despite an attempt of the detection, the vertical synchronization signal during the synchronization signal waiting time after starting the antenna selection at the time point explained above (not-received virtual transmission data is shown by an alternate long and short dash line). Therefore, the preamble detector 223a shifts to a sleep condition after the elapse of the synchronization signal waiting time in the receiving apparatus 20.

After that, the control unit 227 predicts an operation start time of an antenna selecting operation on the assumption that transmission data to be received after the transmission data 50-1 is transmitted at the maximum frame rate of the frame rates not predicted yet. Specifically, the maximum value among the plurality of frame rates, stored in the storage unit 226, not predicted yet at this time point is 2 (fps). Therefore, a reception of the transmission data 50 which is predicted to be received next is configured to start at the time when 2 T=0.5 (s) has elapsed after the reception start of the first transmission data 50-1. In this case, the control unit 227 causes the switching unit 221 to operate to start the process of selecting a receiving antenna at the time when the operation start time $T_2$ has elapsed after the synchronization signal detector 223b had detected the vertical synchronization signal of the transmission data 50-1. As shown in FIG. 15, the synchronization signal detector 223b detects a vertical synchronization signal of transmission data 50-2 after the antenna selection at this timing.

As explained above, when the receiving apparatus 20 receives second transmission data (the transmission data 50-2 in FIG. 15), the receiving apparatus 20 performs the same operation as explained above on the assumption that a frame rate of transmission data to be received next is the maximum value, 4 (fps) in the case shown in FIG. 13, of the plurality of frame rates which can be set.

Next, reference will be made to a case, different from the case shown in FIG. 15, where the synchronization signal detector 223b cannot detect the vertical synchronization signal of the second transmission data even by setting the frame rate to 2 (fps). In this case, the receiving apparatus 20 sets a frame rate of transmission data to be received after the transmission data 50-1 to 1 (fps) and starts the antenna selecting operation at the time point when the operation start time $T_3$ has elapsed after the detection of the vertical synchronization signal of the transmission data 50-1. After that, when the synchronization signal detector 223b detects the vertical synchronization signal within the synchronization signal waiting time after the start of the detection, the receiving apparatus 20 sets a frame rate of next transmission data to 4 (fps) (the maximum value of the plurality of frame rates which can be set) and performs the same operation as explained above.

In contrast, when transmission data cannot be obtained by setting the frame rate to 1 (fps), the receiving apparatus 20 sets the frame rate of transmission data to be received after the transmission data 50-1 to 0.5 (fps) and starts the antenna selecting operation at the time point when the operation start time $T_4$ has elapsed after the detection of the vertical synchronization signal of the transmission data 50-1. After that, when the synchronization signal detector 223b detects the vertical synchronization signal within the synchronization signal waiting time after starting the detection, the receiving apparatus 20 sets a frame rate of next transmission data to 4 (fps) (the maximum value among the plurality of frame rates which can be set) and performs the same operation as explained above. In contrast, when the vertical synchronization signal cannot be detected within the synchronization signal waiting time explained above even by setting the frame rate of the transmission data to be received after the transmission data 50-1 to 0.5 (fps), the receiving apparatus 20 determines itself to be in the defect condition and performs the operation explained in the first embodiment (see FIGS. 4 and 6).

According to the above-described third embodiment of the present invention, it is possible to suppress power consumption similarly to the first embodiment explained above.

Besides, according to the third embodiment, since the process is performed on the assumption of receiving transmission data at all frame rates when a plurality of frame rates different from each other are stored in the storage unit, it is possible to surely receive even transmission data whose frame rate changes.

Similarly to the second embodiment, the preamble period may be divided into two, i.e., the first and the second preambles in the transmission data in the third embodiment. In this case, when the receiving apparatus in the initial condition or in the defect condition first detects a preamble, the receiving apparatus may perform the same operation as the second embodiment (see FIGS. 11 and 12).

Fourth Embodiment

FIG. 16 is a schematic diagram of a configuration of transmission data that a capsule endoscope transmits to a receiving apparatus in a capsule endoscope system according to a fourth embodiment of the present invention. A configuration of the capsule endoscope system according to the fourth embodiment is the same as that of the capsule endoscope system 1 explained above.

Transmission data 70 shown in FIG. 16 includes a preamble 71 and image data 72. The image data 72 is serial data including, in chronological order, a horizontal synchronization signal 73-0, data 74-0, a horizontal synchronization signal 73-1, data 74-1, a horizontal synchronization signal 73-2, . . . , a horizontal synchronization signal 73-n, and data 73-n. In the horizontal synchronization signals 73-1, 73-2, . . . , and 73-n, information indicating the number of remaining lines is added. For example, information that the number of remaining lines is "n" is added in the horizontal synchronization signal 73-1. Similarly, information that the number of remaining lines is "1" and information concerning a blank time is added in the horizontal synchronization signal 73-n.

In the receiving apparatus 20 having received the transmission data 70 having the configuration explained above, the synchronization signal detector 223b detects a horizontal synchronization signal 73-i (i=1, 2, . . . , n) of the transmission data 70 to obtain the number of remaining lines and the blank time. The control unit 227 predicts a period of time during which the preamble period of next transmission data 70 is transmitted based on the number of remaining lines and the blank time included in the horizontal synchronization signal 73-i. After that, the control unit 227, after obtaining the transmission data 70 and becoming a sleep condition, selects a receiving antenna during a preamble period of next frame based on a result of the prediction explained above. The receiving apparatus 20 then performs the detection of a vertical synchronization signal by the synchronization signal detector 223b without activating the preamble detector 223a.

According to the fourth embodiment of the present invention explained above, since information concerning the number of remaining lines and the blank time is added in a horizontal synchronization signal, it is possible not only to receive transmission data even when a frame rate of the transmission data changes but also to cause the preamble detector to shift to a sleep condition at a proper moment. Hence, it is possible to suppress power consumption and surely receive transmission data by using an appropriate receiving antenna.

Here, information indicating an order of lines may be added in a horizontal synchronization signal instead of the number of remaining lines. In this case, it is necessary to further add information to the effect of being the last line in the last horizontal synchronization signal.

Moreover, information of a blank time may be added in all horizontal synchronization signals. In this case, the control unit is able to predict an operation timing with respect to transmission data to be received next only by referring to additional information of one horizontal synchronization signal.

While reference has been made to the embodiments of the present invention, the present invention should not be limited only to the four embodiments. In other words, the present invention includes various embodiments and the likes not mentioned here.

Notes

A receiving apparatus that includes: a plurality of receiving antennas capable of receiving transmission data which is wirelessly and continuously transmitted frame by frame, and includes a preamble at a head and a synchronization signal at a head of main data following the preamble, information concerning a preamble period of transmission data to be transmitted after the transmission data being added in the synchronization signal; a switching unit that selectively switches a connection to any one of the plurality of receiving antennas; a preamble detector that detects the preamble of the transmission data output via a receiving antenna which is connected by the switching unit; a synchronization signal detector that detects the synchronization signal of the transmission data output via the receiving antenna which is connected by the switching unit; and a control unit that, when the preamble detector detects the preamble, causes the preamble detector to be in a sleep condition, predicts a preamble period of transmission data to be detected next by using the information added in the synchronization signal, causes the switching unit to sequentially switch the connection to the plurality of receiving antennas based on a result of the prediction, and selects a receiving antenna whose received strength is the largest.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A receiving apparatus for receiving transmission data, the receiving apparatus comprising:
    a plurality of receiving antennas capable of receiving the transmission data from a capsule medical device which is wirelessly transmitted frame by frame from the capsule medical device, the transmission data including a preamble at a head and a vertical synchronization signal at a head of main data following the preamble;
    a switching unit that selectively switches a connection to any one of the plurality of receiving antennas based on a signal strength of each of the plurality of receiving antennas;
    a preamble detector that detects the preamble of the transmission data output via a receiving antenna which is connected by the switching unit;
    a vertical synchronization signal detector that detects the vertical synchronization signal of the transmission data output via the receiving antenna which is connected by the switching unit; and
    a control unit for controlling the switching unit, preamble detector and vertical synchronization detector and that controls whether or not to cause the preamble detector to be in a sleep condition based on a detection result by the preamble detector;
    wherein when the preamble detector detects the preamble, the control unit causes the vertical synchronization signal detector to detect the vertical synchronization signal of the transmission data, and thereafter causes the preamble detector to shift to the sleep condition to suppress power consumption.

2. The receiving apparatus according to claim 1, wherein the control unit controls selecting any one of the plurality of receiving antennas.

3. A capsule endoscope system, comprising:
    the receiving apparatus according to claim 1; and
    a capsule endoscope that is introduced into a body of a subject and wirelessly transmits transmission data including image data obtained by capturing images of an inside of the subject, to the receiving apparatus.

4. The receiving apparatus according to claim 1, wherein if the preamble detector is not able to detect the preamble during a specified period of time after activation of the preamble detector, the control unit causes the preamble detector to shift to the sleep condition.

5. A receiving apparatus for receiving transmission data, the receiving apparatus comprising:
    a plurality of receiving antennas capable of receiving the transmission data from a capsule medical device which is wirelessly transmitted frame by frame from the capsule medical device, the transmission data including a preamble at a head and a vertical synchronization signal at a head of main data following the preamble;
    a switching unit that selectively switches a connection to any one of the plurality of receiving antennas based on a signal strength of each of the plurality of receiving antennas;
    a preamble detector that detects the preamble of the transmission data output via a receiving antenna which is connected by the switching unit;
    a control unit for controlling the switching unit, preamble detector and a vertical synchronization detector and that controls whether or not to cause the preamble detector to be in a sleep condition based on a detection result by the preamble detector, and controls selecting any one of the plurality of receiving antennas;
    the vertical synchronization signal detector that detects the vertical synchronization signal of the transmission data output via the receiving antenna which is connected by the switching unit; and
    a storage unit that stores a frame rate of the transmission data, wherein
    when the preamble detector detects the preamble, the control unit causes the preamble detector to be in the sleep condition, predicts a preamble period of transmission data to be detected next by using the frame rate stored in the storage unit, and causes the switching unit to sequentially switch the connection to the plurality of receiving antennas based on a prediction result to select a receiving antenna whose received strength is largest.

6. The receiving apparatus according to claim 5, wherein the control unit causes the synchronization signal detector to detect the synchronization signal of the transmission data after selecting the receiving antenna whose received strength is the largest.

7. The receiving apparatus according to claim 6, wherein
    the storage unit stores, as the frame rate of the transmission data, a plurality of frame rates whose values are different from one another,
    the control unit
        (a) predicts the preamble period of the transmission data to be detected next by using a maximum frame rate in frame rates not predicted yet among the plurality of frame rates stored in the storage unit,
        (b) selects a receiving antenna whose received strength is the largest based on the prediction result in the process (a), and
        (c) causes the synchronization signal detector to detect the synchronization signal, wherein
    the control unit performs the processes from (a) to (c) repeatedly, and
    when the synchronization signal detector detects the synchronization signal in the process (c), the control unit sets the frame rates not predicted yet in the process (a) to be performed immediately after the process (c) as the plurality of frame rates.

8. A receiving apparatus for receiving transmission data, the receiving apparatus comprising:
    a plurality of receiving antennas capable of receiving the transmission data from a capsule medical device which is wirelessly transmitted frame by frame from the capsule medical device, the transmission data including a preamble at a head;

a switching unit that selectively switches a connection to any one of the plurality of receiving antennas based on a signal strength of each of the plurality of receiving antennas;

a preamble detector that detects the preamble of the transmission data output via a receiving antenna which is connected by the switching unit;

a control unit for controlling the switching unit and the preamble detector and that controls whether or not to cause the preamble detector to be in a sleep condition based on a detection result by the preamble detector, and controls selecting any one of the plurality of receiving antennas;

wherein in an initial condition where the preamble detector does not detect the preamble after a power activation or in a defect condition where the preamble is not detected for equal to or more than a specified period of time after a most recent detection of the preamble, after the control unit causes the switching unit to sequentially switch the connection to the plurality of receiving antennas to select a receiving antenna whose received strength is largest, the control unit activates the preamble detector, and causes the preamble detector to be in a sleep condition for a specified sleep time if the preamble detector does not detect the preamble even after a lapse of a maximum waiting time after being activated, wherein a total sum of an antenna selection time required for selecting the receiving antenna whose received strength is the largest, the maximum waiting time, and the sleep time is shorter than a reception time of the preamble in a single piece of transmission data.

9. The receiving apparatus according to claim 8, wherein the preamble includes
a first preamble which is a first half of a period of the preamble divided into two along time and
a second preamble which includes information distinguishable from the first preamble and is a second half of the period of the preamble divided into two along time, wherein
the control unit causes the switching unit to sequentially switch the connection to the plurality of receiving antennas to select the receiving antenna whose received strength is the largest when the preamble detector detects the first preamble.

10. The receiving apparatus according to claim 9, wherein a reception time of the first preamble is equal to or less than a reception time of the second preamble.

\* \* \* \* \*